(12) United States Patent
White (10) Patent No.: US 11,237,125 B2
(45) Date of Patent: Feb. 1, 2022

(54) DETERMINING HEMATOCRIT LEVEL OF A BLOOD SAMPLE

(71) Applicant: Hewlett-Packard Development Company, L.P., Spring, TX (US)

(72) Inventor: Rachel M. White, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 161 days.

(21) Appl. No.: 16/618,840

(22) PCT Filed: Jul. 17, 2017

(86) PCT No.: PCT/US2017/042410
§ 371 (c)(1),
(2) Date: Dec. 3, 2019

(87) PCT Pub. No.: WO2019/017882
PCT Pub. Date: Jan. 24, 2019

(65) Prior Publication Data
US 2020/0096464 A1    Mar. 26, 2020

(51) Int. Cl.
*G01N 27/06* (2006.01)
*G01N 33/49* (2006.01)

(52) U.S. Cl.
CPC ............. *G01N 27/06* (2013.01); *G01N 33/49* (2013.01)

(58) Field of Classification Search
CPC ................................ G01N 27/06; G01N 33/49
See application file for complete search history.

(56) References Cited

U.S. PATENT DOCUMENTS

| 6,794,877 | B2 | 9/2004 | Blomberg et al. |
| 8,865,074 | B2 | 10/2014 | Kwak et al. |
| 2011/0289043 | A1* | 11/2011 | Suresh .................... A61P 37/06 706/52 |

(Continued)

FOREIGN PATENT DOCUMENTS

| CN | 103913489 | 7/2014 |
| EP | 0417796 | 3/1991 |

(Continued)

OTHER PUBLICATIONS

Lei et al., Real-Time Electrical Impedimetric Monitoring of Blood Coagulation Process under Temperature and Hematocrit Variations Conducted in a Microfluidic Chip, PLOS/One Tenth Anniversary, http://journals.plos.org/plosone/article?id=10.1371/journal.pone.0076243, Oct. 7, 2013, 8 pages.

(Continued)

*Primary Examiner* — Alvaro E Fortich
*Assistant Examiner* — Zannatul Ferdous
(74) *Attorney, Agent, or Firm* — Thorpe North & Western LLP (57) ABSTRACT

An apparatus includes a die having a receiving area for a blood sample. A chamber is mounted on the die and fluidically coupled to the receiving area to process the blood sample. The chamber includes a set of electrodes that applies a voltage to the blood sample. A hematocrit level of the blood sample is determined based on a change in impedance across the set of electrodes after the voltage is applied.

17 Claims, 5 Drawing Sheets

(56) References Cited

U.S. PATENT DOCUMENTS

| | | | | |
|---|---|---|---|---|
| 2013/0110405 A1* | 5/2013 | Yang | .................. | G01N 33/49 |
| | | | | 702/19 |
| 2014/0014533 A1* | 1/2014 | Yan | .................. | G01N 33/4905 |
| | | | | 205/780.5 |
| 2014/0284223 A1* | 9/2014 | Malecha | ................ | G01N 27/26 |
| | | | | 205/782 |
| 2015/0260705 A1* | 9/2015 | Yang | .................. | G01N 27/06 |
| | | | | 435/29 |
| 2015/0338363 A1 | 11/2015 | Dean, Jr. et al. | | |
| 2016/0178409 A1* | 6/2016 | Tsutsui | ................ | H02J 1/00 |
| | | | | 702/189 |
| 2017/0156648 A1* | 6/2017 | Yang | .................. | G01N 33/49 |

FOREIGN PATENT DOCUMENTS

| | | |
|---|---|---|
| TW | 1472766 | 2/2015 |
| TW | 1481869 | 4/2015 |
| TW | 201520545 | 6/2015 |
| TW | 201532879 | 9/2016 |
| WO | 2016040620 | 3/2016 |

OTHER PUBLICATIONS

International Search Report dated Jul. 17, 2017 for PCT/US2017/042410, Applicant Hewlett-Packard Development Company, L.P.

\* cited by examiner

DETERMINING HEMATOCRIT LEVEL OF A BLOOD SAMPLE

BACKGROUND

Hematocrit is a measure of the volume percentage of red blood cells in a patient sample. Blood is comprised of red and white blood cells suspended in plasma. A patient's hematocrit can be used as an indication of health. A low hematocrit can be the result of bleeding, anemia, or nutritional problems for example. An abnormally high hematocrit can mean dehydration, low availability of oxygen, and heart related issues such as pulmonary embolisms.

DETAILED DESCRIPTION

An apparatus is provided (e.g., microfluidic chip) that measures patient hematocrit levels by electrically detecting the density of red blood cells as they settle over a set of electrodes. Hematocrit is a measure of the red blood cell content of a given blood sample. A capillary (e.g., fingerprick) blood sample is added to a receiving area of a die. The blood sample enters the receiving area of the die and flows into a chamber on the die via capillary action. The chamber includes the set of electrodes and as red blood cells enter the chamber from the receiving area of the die, the cells settle on to the electrodes. Since higher hematocrit samples contain more red blood cells, this translates to more cells entering the chamber and resting on the electrodes which provides a more intense electric signal (e.g., higher current/voltage measurement) in response to the voltage applied to the electrodes. As voltage is applied to the blood sample via the electrodes, impedance is measured (e.g., measurement of electrical parameter from the electrodes) which is analyzed over time. The impedance can be automatically analyzed according to linear or non-linear functions which measure the change in impedance (e.g., slope) as voltage is cycled to the electrodes over time. Other automated analysis can include comparing impedance measurements to stored blood profiles to determine the red blood cell content.

Figure 1:
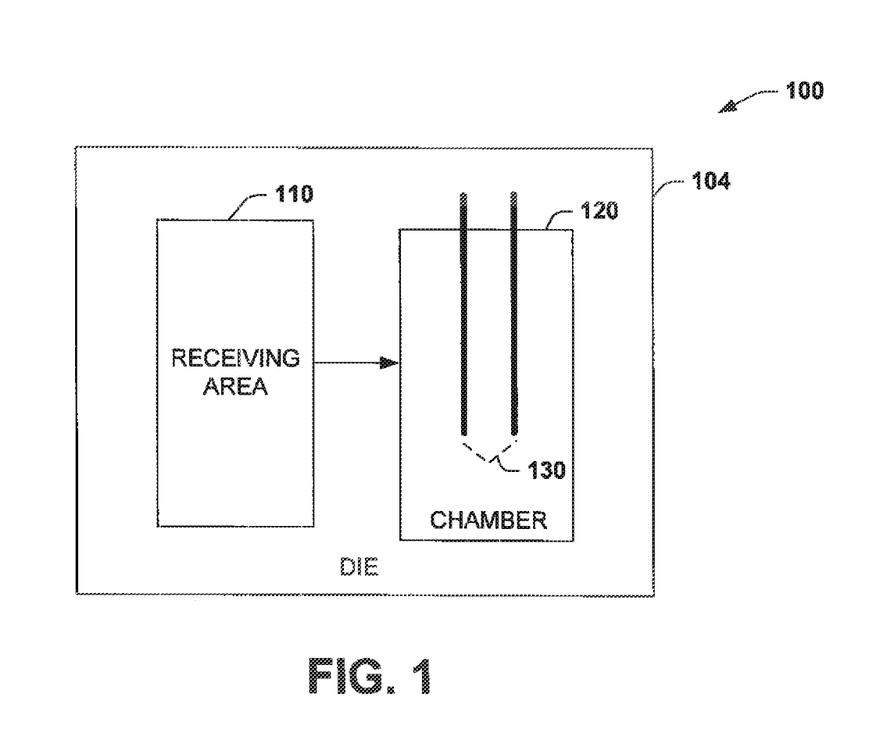
FIG. 1 illustrates an example apparatus to determine hematocrit level of a blood sample.

FIG. 1 illustrates an example apparatus 100 to determine hematocrit level of a blood sample. As used herein the term hematocrit is a measure of the volume percentage of red blood cells in a user blood sample. For example, the volume of red blood cells versus plasma in the blood. The apparatus 100 includes a die 104 having a receiving area 110 for a blood sample. A chamber 120 can be mounted on the die and is fluidically coupled to the receiving area 110 to process the blood sample. The chamber 120 includes a set of electrodes 130 that applies a voltage to the blood sample. A hematocrit level of the blood sample can be determined based on a change in impedance across the set of electrodes 130 after the voltage is applied. As used herein, the term impedance can refer to a resistance or a more complex term that includes resistance, capacitance, and/or or inductance, for example.

With respect to prior systems, hematocrit is typically measured as part of a complete blood count (CBC) but this type test relies on a painful venous draw from a patient and can be very expensive. The apparatus 100 can be implemented as a microfluidic chip that provides a rapid, inexpensive, and portable test that does not utilize a venous blood draw from the patient. Thus, blood tests using the apparatus 100 should be more comfortable for the patient and can be performed in situations when a CBC is not employed. The apparatus 100 can be utilized to perform hematocrit testing as described herein and can be disposed after testing in some example implementations.

The apparatus 100 measures patient hematocrit levels by electrically detecting the density of the red blood cells as they settle over the set of electrodes 130. A capillary (fingerprick) blood sample can be added (e.g., via pipette dispenser) to the receiving area 110 which migrates to the chamber 120 via capillary action or via micro-electromechanical systems such as pumps, for example. As the red blood cells enter the chamber 120, they settle and rest on the electrodes 130. Higher hematocrit samples should contain more red blood cells. This translates to more cells entering the chamber and resting on the electrodes, which yields a more intense electric signal and provides a different impedance profile than samples having higher or lower amounts of red blood cells.

The die 104 can be a silicon substrate or a printed circuit board (PCB), for example. A first portion of the substrate or the PCB of the die 104 can be assigned to the receiving area 110 and a second portion of the substrate or the PCB of the die can be assigned to the chamber 130. The set of electrodes 130 can be fabricated on the substrate or the PCB to apply the voltage to the blood sample. An on or off chip processing circuit (see e.g., FIG. 4) can be provided to apply the voltage to the electrodes 130 and determine the hematocrit levels as described herein. The processing circuit can also communicate determined hematocrit levels detected from a given blood sample to other devices (e.g., cell phone, digital assistant) or networks (e.g., Internet database).

The voltage can be applied to the electrodes 130 as an alternating current (AC) voltage or direct current (DC) voltage where the change in impedance is detected by measuring an electrical parameter (e.g., current or voltage) from the set of electrodes in response to the applied voltage. The electrical parameter can include current and/or voltage measurements. For example, current can be measured by measuring the voltage across a small series resistor, a current loop, or current transformer. Voltage can be measured as part of another network such as measuring a voltage drop change across a voltage divider to determine the impedance. The measured electrical parameter can be digitized to construct impedance profiles for further hematocrit analysis. A continuous voltage can be applied to the electrodes 130 however the voltage can be applied as a step function to the set of electrodes to mitigate electrolysis across the set of electrodes and to mitigate degradation of the blood sample. The receiving area 110 can include at least one other channel that feeds at least one other chamber 120 on the die 104 to support other tests than the hematocrit level of the blood sample. For example, one channel in the receiving area 110 can feed a chamber to determine hematocrit levels and another channel in the receiving area can feed a separate chamber to perform other tests on the blood sample.

The apparatus 104 can include a base layer that provides a substrate to support a fluid flow assembly (e.g., integrated assembly for routing and/or testing fluids). The base layer can provide a substrate composed of a single material (e.g., polymer resin) or can provide a substrate assembly of more than one material (e.g., layered materials forming the base layer). In one example, the base layer can be formed as an epoxy molding compound (EMC), such as a thermosetting epoxy polymer resin material. In addition to capillary action to move a blood sample from the receiving area 110 to the chamber 120, the die 130 can include a fluidic actuator (not shown) to control fluid flow across the surface of the die. The fluidic actuator can be implemented as one or more types of actuators. In some examples, a Micro-Electro-Mechanical Systems (MEMS) layer can be formed on a surface of the die 104 to provide a corresponding fluidic actuator. The fluidic actuator can be an electrode actuator, a capillary actuator, or a pump actuator, for example, to control fluid flow across the surface of the die 104. A cover (see e.g., FIG. 2) can be formed over the chamber 120 and can be formed as one or more layers of a Cyclic Olefin Polymer (COP) or Cyclic Olefin Copolymer (COC), for example.

Figure 2:
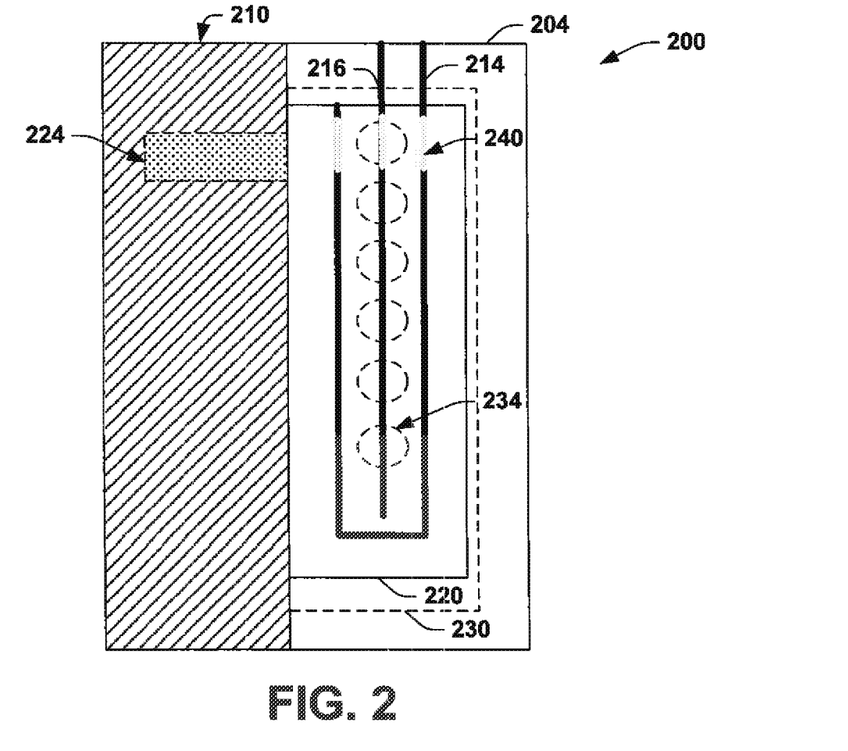
FIG. 2 illustrates a top view of an example apparatus to determine hematocrit level of a blood sample.

FIG. 2 illustrates a top view of an example apparatus 200 to determine hematocrit level of a blood sample. The apparatus 200 includes a die 204 having a receiving area 210 (e.g., slot area over die) for a blood sample. A chamber 220 can be mounted on the die and is fluidically coupled to the receiving area 210 to process the blood sample. The chamber 220 includes a set of electrodes 214 and 216 that applies a voltage to the blood sample (e.g., via on or off chip processing circuit). A hematocrit level of the blood sample can be determined based on a change in impedance across the set of electrodes 214 and 216 after the voltage is applied. As noted previously, the voltage can be applied to the electrodes 214 and 216 as an alternating current (AC) voltage or direct current (DC) voltage where the change in impedance is detected by measuring an electrical parameter from the set of electrodes in response to the applied voltage.

The measured electrical parameter can be digitized by the processing circuit to construct impedance profiles for further hematocrit analysis. In one example, the receiving area 210 can include at least one other channel 224 that feeds at least one other chamber (not shown) on the die 204 to support other tests than the hematocrit level of the blood sample. For example, one channel in the receiving area 210 can feed a chamber to determine hematocrit levels and another channel in the receiving area can feed a separate chamber to perform other tests on the blood sample.

The chamber 220 can include a polymer or copolymer cover 230 that includes an air vent 234 (or vents) to allow air to escape from the chamber and to support capillary action for the blood sample to flow from the receiving area 210 to the chamber. The set of electrodes 214 and 216 provides exposed conductive areas such as the example area shown at 240 to allow the blood sample to be stimulated with electric fields and to be averaged across the conductive areas (e.g., allowing more areas of the blood sample to be exposed to an electric field and providing an average of the exposed sample). As used herein the term exposed conductive area refers to fabricating the electrode 214/216 having portions that provides an un-encapsulated surface and where insulative coating is not applied to the electrode. This increases the sensitivity of the electrodes to provide more accurate measurements. The set of electrodes 214 and 216 can include a ground electrode such as electrode 216 that is surrounded by a power electrode such as electrode 214 to provide the electric fields across the exposed conductive areas of the electrodes. By surrounding the ground plane, a more consistent and intense electric field can be applied to the blood sample to generate an electrical parameter that can be measured to determine an impedance profile to determine the hematocrit level which is described below with respect to FIGS. 3 and 4.

Figure 3:
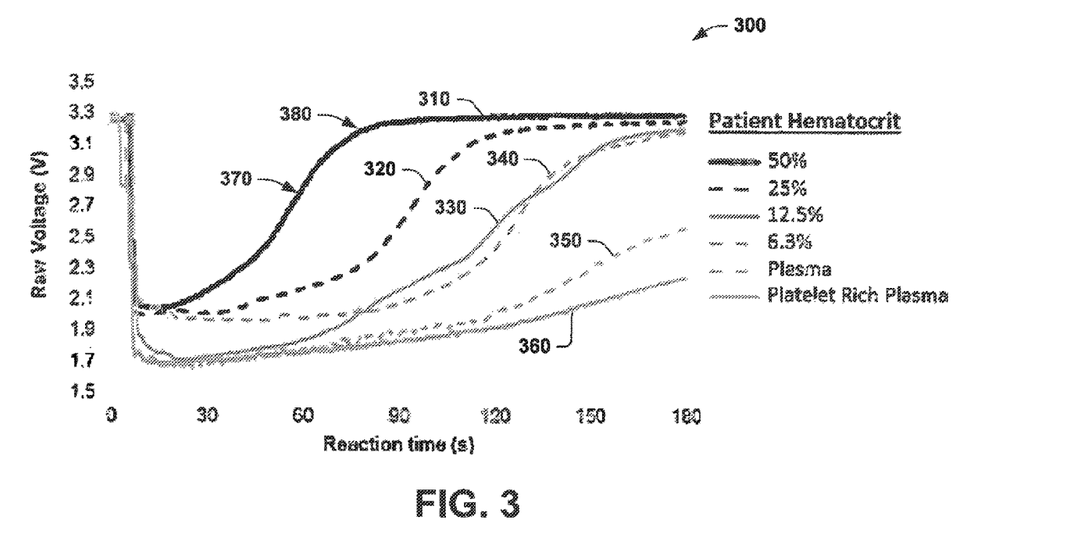
FIG. 3 illustrates a diagram representing example data sets for impedance profiles of different hematocrit blood levels.

FIG. 3 illustrates a diagram 300 representing example data sets for impedance profiles of different hematocrit blood levels. The diagram 300 shows a representative data set from testing different hematocrit levels. The horizontal axis represents time that voltage is applied to a given sample and the horizontal axis is a measure of voltage across a sensing element (e.g., sense series resistor or sense voltage divider) as voltage is applied to the blood sample. Thus, the different profiles shown representing different hematocrit levels show how impedance changes over time as the voltage is applied to the sample. A line 310 represents an impedance profile having a hematocrit level of about 50%. A line 320 represents an impedance profile having a hematocrit level of about 25%. A line 330 represents an impedance profile having a hematocrit level of about 12.5%. A line 340 represents an impedance profile having a hematocrit level of about 6.3%. A line 350 represents an impedance profile of a plasma and line 360 represents an impedance profile of a platelet rich plasma (PRP). Other profile types are possible.

In this example, the measurement system used a DC method of measurement however as noted previously, AC voltages can be applied. An initial voltage is applied and the voltage across the sensing elements associated with the electrodes is measured to indicate the changes in resistivity (or impedance) of the sample. As the sample wets the electrodes, the measured voltage can drop initially. Red blood cells are generally resistive compared to the plasma that surrounds them. As more red blood cells come to rest on the electrodes, the measured voltage generally increases. The data shown in the diagram 300 suggests that the rate of increase in voltage and the final maximum voltage measured are proportional to the patient's hematocrit. As the concentration of red blood cells increases, so does the measured sense voltage. Both PRP and plasma have substantially no red blood cells thus the hematocrit level is about 0%.

The measured impedance profiles can be compared to stored predetermined impedance profiles to determine hematocrit levels where points along a given blood sample having a profile are measured and compared to the stored profile. Interpolation can be used to determine differences between stored profile points along a given profile curve with measured points along a given sample of a measured impedance curve. Mathematical functions can be applied such as applying a linear function to linear points of the profiles such as shown at 370 (e.g., analyzing slope using y=mx+b). Non-linear functions (e.g., logarithmic or natural logarithmic) can be applied to analyze non-linear portions of the curve such as shown at 380.

Figure 4:
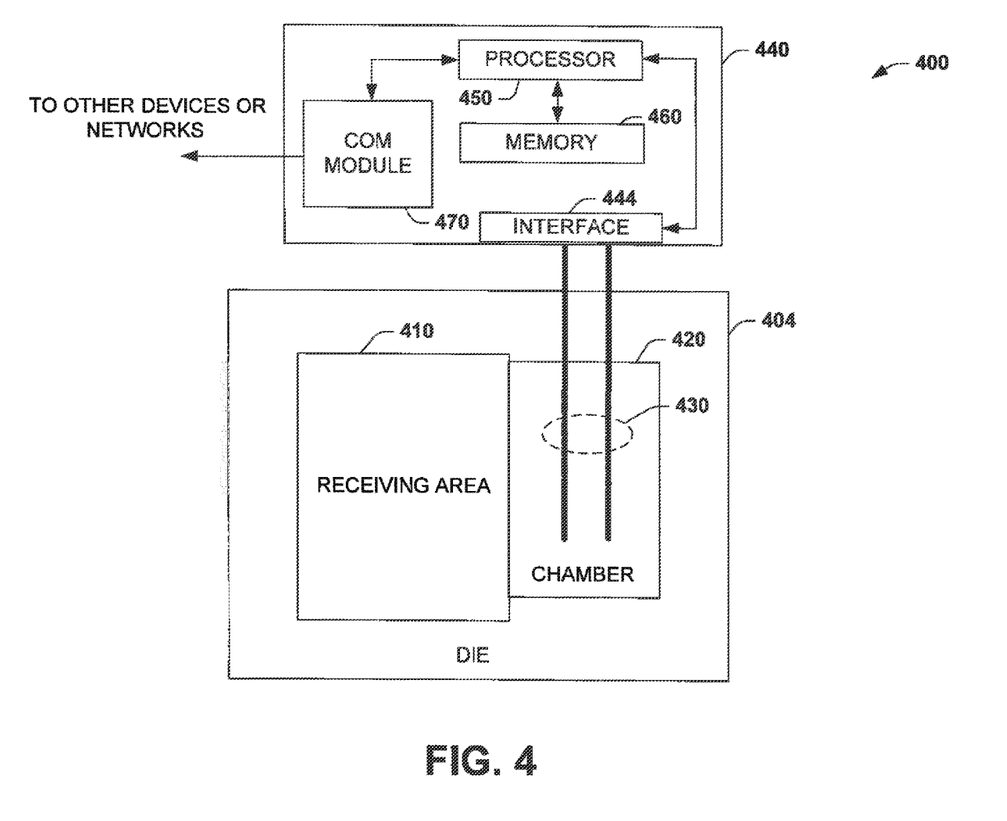
FIG. 4 illustrates an example system to determine hematocrit level of a blood sample.

FIG. 4 illustrates an example system 400 to determine hematocrit level of a blood sample. The system 400 includes a die 404 having a receiving area 410 for a blood sample. A chamber 420 can be mounted on the die and is fluidically coupled to the receiving area 410 to process the blood sample. The chamber 420 includes a set of electrodes 430 that provides a voltage to the blood sample. A processing circuit 440 includes an interface 444 to apply the voltage to the set of electrodes 430. A processor 450 executes instructions from a memory 460 to control the interface 444. The instructions cause the processor 450 to determine a hematocrit level of the blood sample based on a detected change in impedance across the set of electrodes 430 after the voltage is applied via the interface 444. Although not shown, the interface 444 can include a power source to apply the voltage to the electrodes and a detector circuit (e.g., sense resistor or voltage divider) to measure an electrical parameter in response to the applied voltage to determine the impedance.

The instructions in the memory 460 can cause the processor 450 to apply a step voltage to the set of electrodes 430 via the interface 444 and to record a series of impedance measurements from the detector circuit over time to generate an impedance profile of the blood sample. The impedance profile can be compared by the processor 450 to a linear function, a non-linear function, or a look-up table representing predetermined impedance profiles that correlate a hematocrit level associated with the predetermined impedance profiles to the impedance profile of the blood sample (e.g., comparing points along a measured impedance curve to points along a stored curve). The predetermined impedance profile can include past measurements from a given user that provides the blood sample to enable the processor 450 to calibrate the blood sample to the given user. For example, a past hematocrit measurement can be used to adjust the processing of the blood sample to account for past hematocrit levels from a given patient. As shown, a communication module 470 (e.g., wireless communications module) controlled by the processor 450 can be employed to communicate the hematocrit level of the blood sample to at least one other device or network. One or more portions of the processing circuit 440 can be implemented outside of the die 404 in some examples. In other examples, one or more portions of the processing circuit 440 can be implemented on the die 404.

Figure 5:
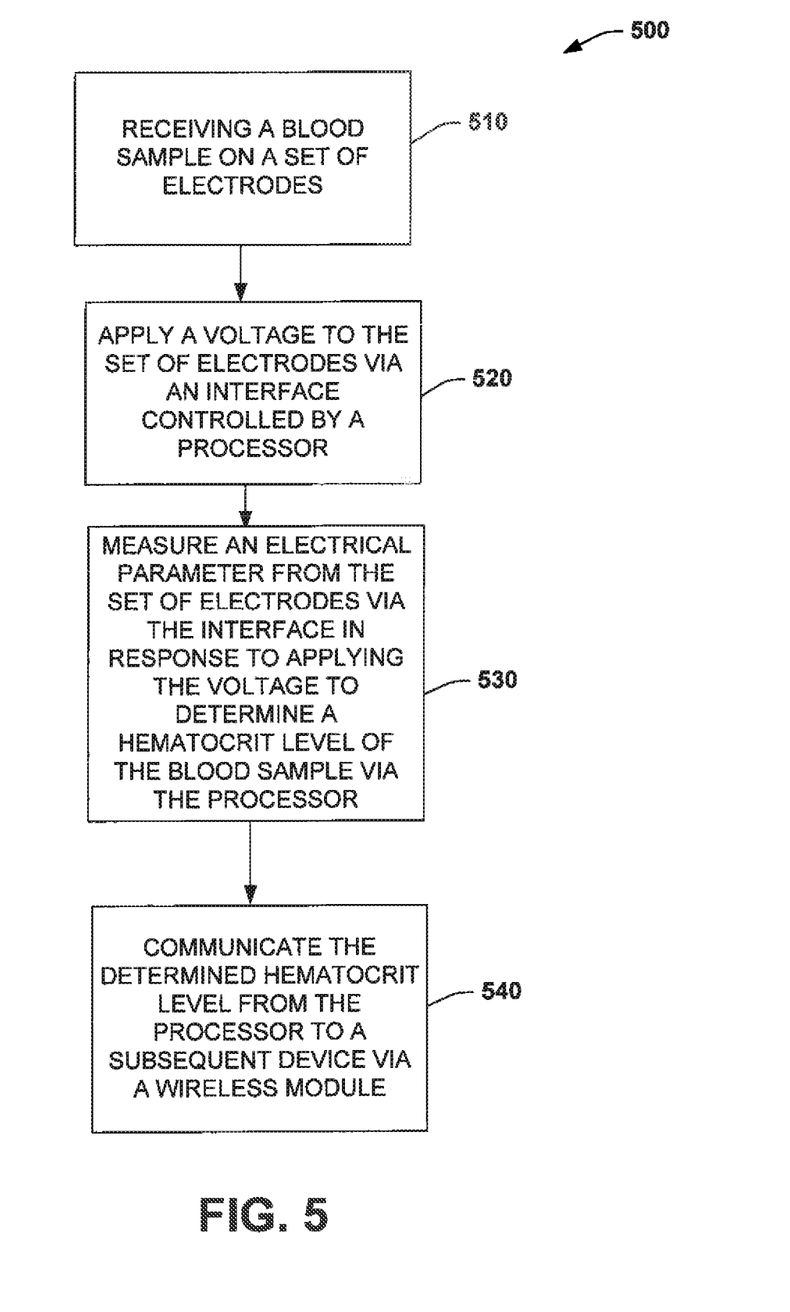
FIG. 5 illustrates an example method to determine hematocrit level of a blood sample.

In view of the foregoing structural and functional features described above, an example method will be better appreciated with reference to FIG. 5. While, for purposes of simplicity of explanation, the method is shown and described as executing serially, it is to be understood and appreciated that the method is not limited by the illustrated order, as parts of the method could occur in different orders and/or concurrently from that shown and described herein. Such method can be executed by various components configured as machine readable instructions stored in memory and executable in an integrated circuit or a processor, for example.

FIG. 5 illustrates an example method 500 to determine hematocrit level of a blood sample. At 510, the method 500 includes receiving a blood sample on a set of electrodes (e.g., via receiving area 120 and chamber 130 of FIG. 1). At 520, the method 500 includes applying a voltage to the set of electrodes via an interface controlled by a processor (e.g., via processor 450 and interface 444 of FIG. 4). At 530, the method 500 includes measuring an electrical parameter from the set of electrodes via the interface in response to applying the voltage to determine a hematocrit level of the blood sample via the processor e.g., via processor 450 and interface 444 of FIG. 4). At 540, the method 500 includes communicating the determined hematocrit level from the processor to a subsequent device via a wireless module e.g., via processor 450 and communication module 470 of FIG. 4). The method 500 can also include comparing an impedance profile from the received blood sample via the processor to a linear function, a non-linear function, or a look-up table representing predetermined impedance profiles that correlate a hematocrit level associated with the predetermined impedance profiles to the impedance profile of the blood sample.

What have been described above are examples. One of ordinary skill in the art will recognize that many further combinations and permutations are possible. Accordingly, this disclosure is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. An apparatus, comprising:
   a die having a receiving area for a blood sampled;
   a chamber fluidically coupled to the receiving area and configured to receive and process the blood sample with a set of electrodes, and
   an on chip processing circuit configured to apply a voltage to the electrodes in contact with the blood sample over time, measure impedance from the set of the electrodes in response to the voltage over time, digitize and determine hematocrit level of the blood sample based on a change in the impedance across the set of electrodes after the voltage is applied.

2. The apparatus of claim 1, wherein the die includes an area assigned to the chamber and the set of electrodes is fabricated on the die.

3. The apparatus of claim 1, wherein the on chip processing circuit is configured to apply the voltage as an alternating current (AC) voltage.

4. The apparatus of claim 3, wherein the on chip processing circuit is configured to apply the voltage as a step function to mitigate electrolysis across the set of the electrodes and to mitigate degradation of the blood sample.

5. The apparatus of claim 1, wherein the receiving area is coupled to a fluidic channel that feeds a testing chamber.

6. The apparatus of claim 1, wherein the die further comprises a fluidic actuator operable to cause the blood sample to flow from the receiving area to the chamber.

7. The apparatus of claim 1, wherein the set of the electrodes has an un-encapsulated surface in the chamber providing an exposed conductive area in the chamber and wherein the set of electrodes includes a ground electrode surrounded by a power electrode in an area of the chamber.

8. A system, comprising:
   a die having a receiving area for a blood sample;
   a chamber fluidically coupled to the receiving area and configured to receive the blood sample from the receiving area and process the blood sample with a set of electrodes;
   and
   a processing circuit including an interface, wherein the processing circuit is configured to execute instructions from a memory to control the interface, wherein the interface is configured to apply the voltage to the set of electrodes, and wherein the instructions cause the processor to determine a hematocrit level of the blood sample based on a detected change in impedance across the set of electrodes after the voltage is applied.

9. The system of claim 8, wherein the interface further comprises a power source to apply the voltage to the set of electrodes and a detector circuit configured to measure an electrical parameter after the voltage is applied.

10. The system of claim 9, wherein the instructions cause the processor to apply a step voltage to the set of electrodes via the interface and to record a series of impedance measurements from the detector circuit over time to generate an impedance profile of the blood sample.

11. The system of claim 10, wherein the processor is configured to compare the impedance profile of the blood sample with a linear function, a non-linear function, or a look-up table representing a predetermined impedance profile correlating a hematocrit level of the predetermined impedance profile to the impedance profile of the blood sample.

12. The system of claim 11, wherein the predetermined impedance profile includes past measurements from a source of the blood sample to enable the processor to calibrate the blood sample to the source.

13. The system of claim 8, further comprising a communication module controlled by the processor and configured to communicate the hematocrit level of the blood sample to another device or network.

14. A method, comprising:
receiving a blood sample in a chamber, wherein the chamber includes a set of electrodes;
applying a voltage to the set of electrodes via an interface controlled by a processor;
measuring the impedance from the set of electrodes via the interface in response to the voltage;
processing the impedance by a processing circuit to determine a hematocrit level of the blood sample based on a change in impedance; and
communicating the hematocrit level from the processor to a subsequent device via a wireless module.

15. The system of claim 14, wherein the processing circuit is configured to compare an impedance profile of the blood sample to a linear function, a non-linear function, or a look-up table representing a predetermined impedance profile and is configured to correlate a hematocrit level of the predetermined impedance profile to the hematocrit level of the impedance profile of the blood sample.

16. The apparatus of claim 1, wherein the on chip processing circuit is configured to apply the applied voltage as a direct current (DC) voltage.

17. The apparatus of claim 1, wherein the die is a silicon substrate or a printed circuit board (PCB).

* * * * *